(12) United States Patent
Ren

(10) Patent No.: US 9,632,042 B2
(45) Date of Patent: Apr. 25, 2017

(54) SINGLE CRYSTAL QUARTZ CHIPS FOR PROTEIN CRYSTALLIZATION AND X-RAY DIFFRACTION DATA COLLECTION AND RELATED METHODS

(71) Applicant: Renz Research, Inc., Westmont, IL (US)

(72) Inventor: Zhong Ren, Westmont, IL (US)

(73) Assignee: RENZ RESEARCH, INC., Westmont, IL (US)

( * ) Notice: Subject to any disclaimer, the term of this patent is extended or adjusted under 35 U.S.C. 154(b) by 149 days.

(21) Appl. No.: 14/502,198

(22) Filed: Sep. 30, 2014

(65) Prior Publication Data

US 2015/0117611 A1 Apr. 30, 2015

Related U.S. Application Data

(60) Provisional application No. 61/895,536, filed on Oct. 25, 2013.

(51) Int. Cl.
*G01N 23/207* (2006.01)
*G01N 23/20* (2006.01)

(52) U.S. Cl.
CPC ..... *G01N 23/207* (2013.01); *G01N 23/20025* (2013.01)

(58) Field of Classification Search
CPC .......................... G01N 23/20; G01N 23/20025
See application file for complete search history.

(56) References Cited

U.S. PATENT DOCUMENTS

| 5,390,230 A * | 2/1995 | Chang | G01N 23/20025 378/79 |
| 2009/0010388 A1* | 1/2009 | Stahly | G01N 21/253 378/79 |
| 2010/0140497 A1* | 6/2010 | Damiano, Jr. | B01L 3/508 250/440.11 |

OTHER PUBLICATIONS

Axford et al., "In situ macromolecular crystallography using microbeams", Acta Cryst., 2012, D68, pp. 592-600.
Bingel-Erlenmeyer et al., "SLS Crystallization Platform at Beamline X06DA—A Fully Automated Pipeline Enabling in Situ X-ray Diffraction Screening", Crystal Growth & Design, 2011, 11, pp. 916-923.

(Continued)

*Primary Examiner* — Hoon Song
(74) *Attorney, Agent, or Firm* — Chen Yoshimura LLP

(57) ABSTRACT

A crystallization device for in situ x-ray diffraction of biological samples includes a flat plate made of single crystal quartz, silicon or sapphire and having an array of wells or lanes defined on the plate. The crystallization device may be in the form of a cover slide used with a crystallization plate in a vapor diffusion setup. Also disclosed is a method for preparing biological samples for crystallization and x-ray diffraction, including: obtaining a crystallization device made of single crystal quartz, silicon or sapphire; loading a solution containing biological molecules onto the crystal support device; maintaining the solution in a crystal growth environment to grow crystals of the biological molecules; removing the crystal support device carrying the crystals from the crystal growth environment; exposing the crystals carried on the crystal support device to an X-ray beam; and recording X-ray diffracted by the biological crystals.

12 Claims, 7 Drawing Sheets

(56) References Cited

OTHER PUBLICATIONS

Jacquamet et al., "Automated Analysis of Vapor Diffusion Crystallization Drops with an X-Ray Beam", Structure, vol. 12, pp. 1219-1225, Jul. 2004.

Kisselman et al., "X-CHIP: an integrated platform for high-throughput protein crystallization and on-the-chip X-ray diffraction data collection", Acta Cryst., 2011, D67, pp. 533-539.

Le Mare et al., "In-plate protein crystallization, in situ ligand soaking and X-ray diffraction", Acta Cryst., 2011, D67, pp. 747-755.

Dhouib et al., "Microfluidic chips for the crystallization of biomacromolecules by counter-diffusion and on-chip crystal X-ray analysis", Lab Chip, 2009, 9, pp. 1412-1421.

Gerdts et al., "The plug-based nanovolume Microcapillary Protein Crystallization System (MPCS)", Acta Cryst., 2008, D64, pp. 1116-1122.

Hansen et al., "A Microfluidic Device for Kinetic Optimization of Protein Crystallization In Situ Structure Determination", J. Am. Chem. Soc., 2006, vol. 128, No. 10, pp. 3142-3143.

Perry et al., "Microfluidic Generation of Lipidic Mesophases for Membrane Protein Crystallization", Crystal Growth & Design, vol. 9, No. 6, 2009, pp. 2566-2569.

Hampton Research, "Hanging Drop Vapor Diffusion Crystallization", https://hamptonresearch.com/documents/growth_101/3.pdf, 2 pages, printed from the internet.

Hampton Research, "Sitting Drop Vapor Diffusion Crystallization", https://hamptonresearch.com/documents/growth_101/4.pdf, 3 pages, printed from the internet.

Hampton Research, "Linbro Plate", http://hamptonresearch.com/product_detail.aspx?cid=10&sid=180&pid=114, 1 page, printed from the Internet on Sep. 30, 2014.

* cited by examiner

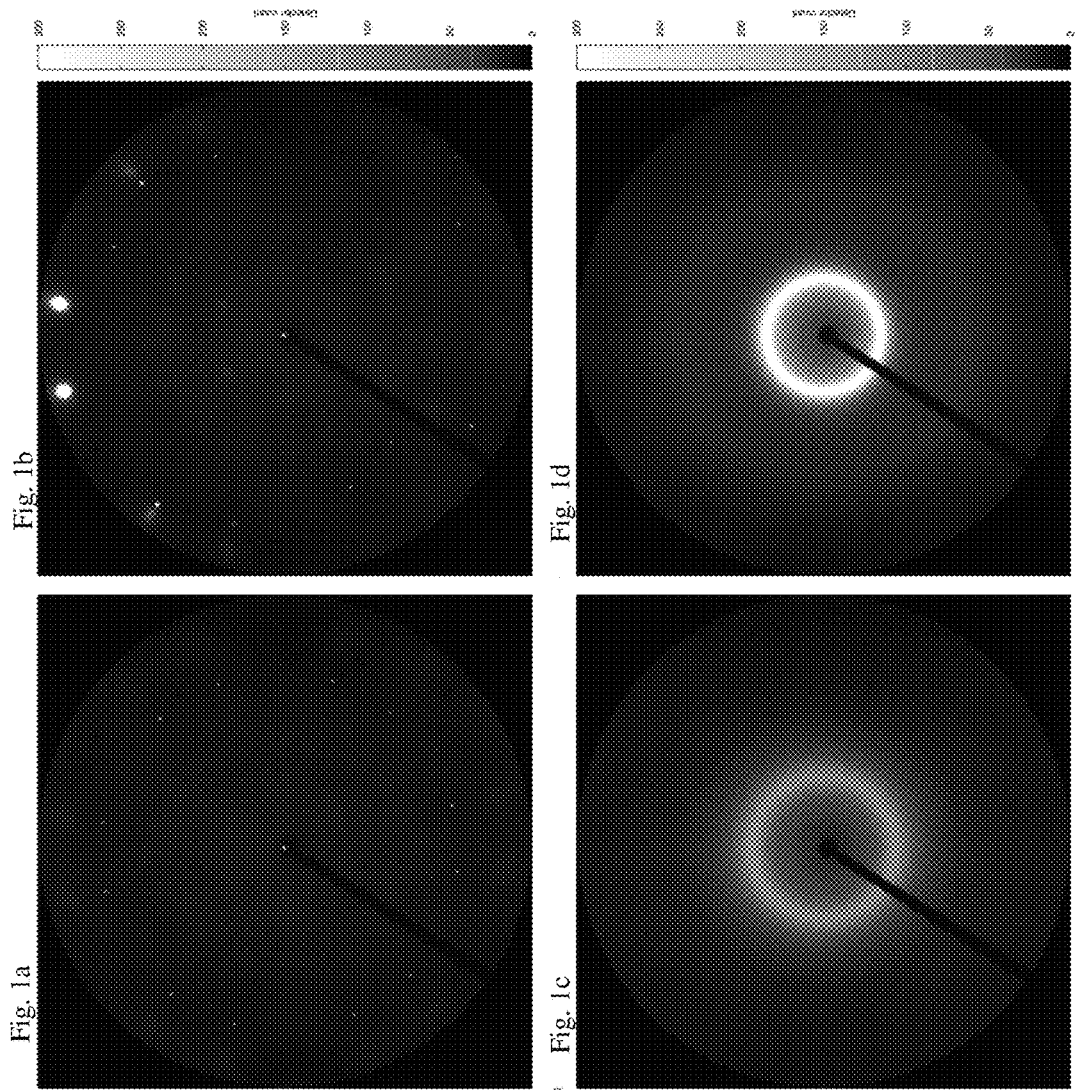

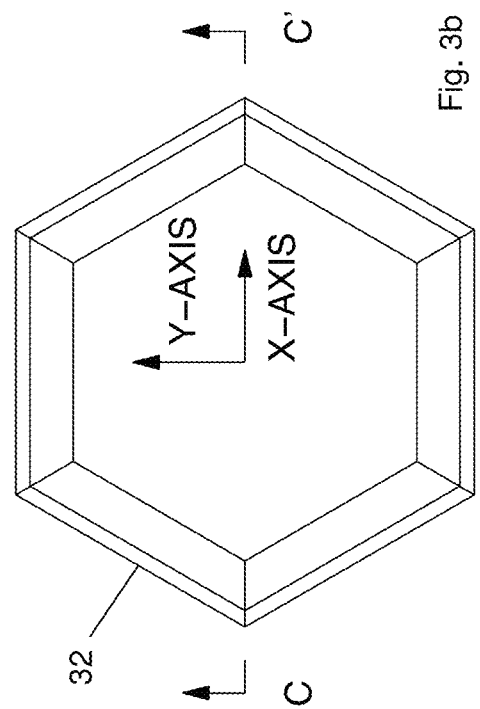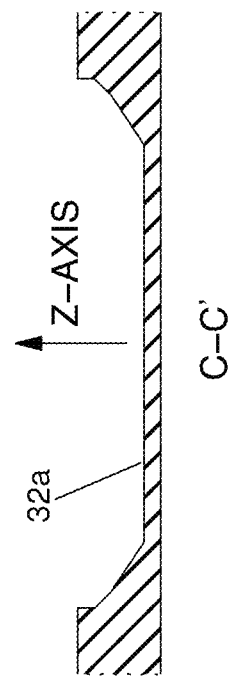

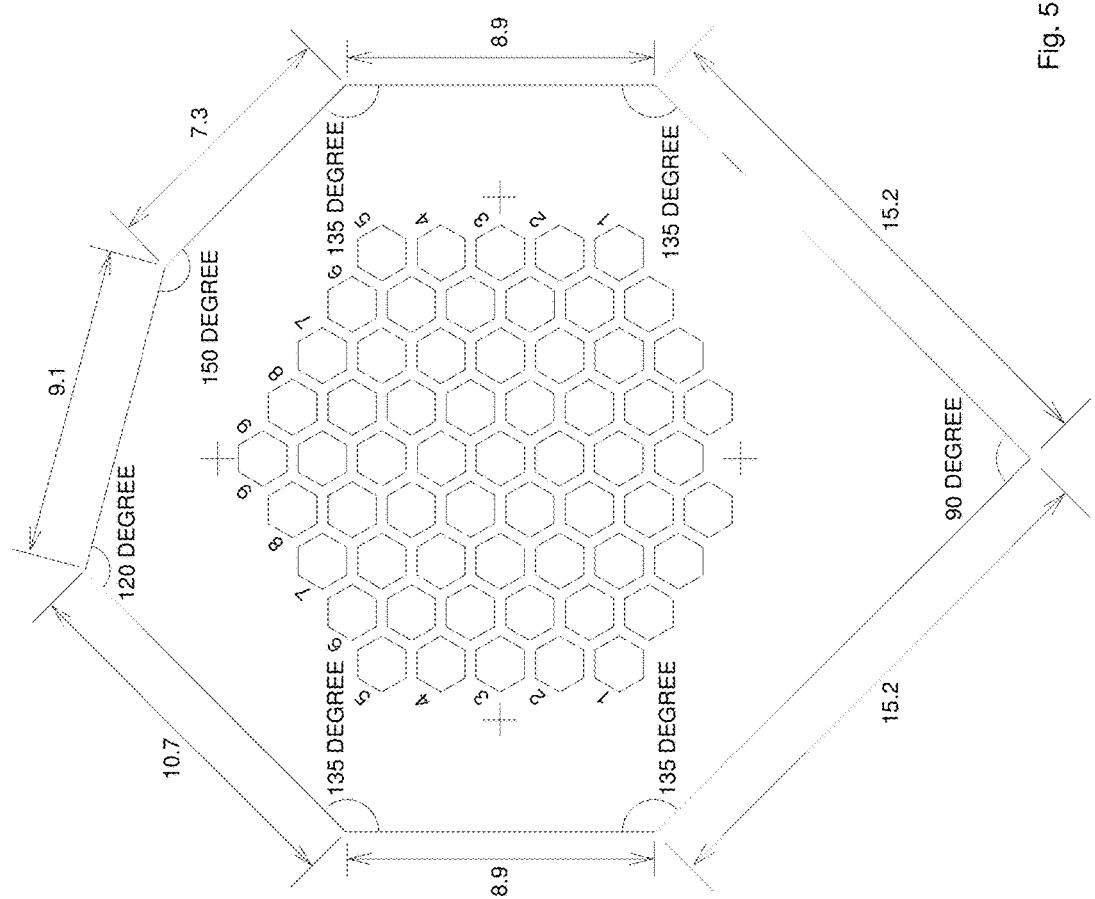

SINGLE CRYSTAL QUARTZ CHIPS FOR PROTEIN CRYSTALLIZATION AND X-RAY DIFFRACTION DATA COLLECTION AND RELATED METHODS

BACKGROUND OF THE INVENTION

Field of the Invention

This invention relates to protein crystallography, and in particular, it relates to single crystal quartz (or other crystal) chips used for protein crystal growth and X-ray diffraction data collection.

Description of the Related Art

Protein crystallography has greatly enriched our knowledgebase of protein structures by providing intricate details of many complicated molecular systems of life. Most recent advances are direct results of rapid progresses in structural genomics projects and wide applications of protein crystallography in many disciplines of life sciences. Protein Data Bank (PDB) is currently expanding at an annual rate greater than 10%. Many exciting new advances in biology demand even more powerful techniques to elucidate changes in protein structures as they function. For example, collection of solar energy by plants and photosynthetic bacteria; oxygenic photosynthesis to produce carbohydrates from carbon dioxide, water, and sun light; visual perception; and other environmental light perceptions to regulate biological processes and circadian rhythms all involve structural changes in proteins and their cofactors, many of which involve ultrafast molecular events. Better understanding of these fundamental processes at the molecular level would have broad and far-reaching impacts on areas of energy, agricultural, environmental, and biomedical sciences.

Indirect observations of protein structural changes have been inferred from comparisons of protein structures stabilized in different static states, for example, the open and closed states of ion channels. In an extreme case, nearly 300 hemoglobin structures have been compared simultaneously using an advanced numerical procedure. The resulting extensive reaction trajectory that twists and turns through several distinct states has shed light into the structural mechanism of cooperative oxygen binding and releasing.

More direct observations of structural changes require datasets collected before and after a deliberate alternation of the protein structure in crystal, such as soaking with a small molecular reagent. A more convenient, thus more practical, reagent to deliver into crystals is light. A temperature scanning technique based on cryocrystallography showed that multiple structural species of a red-light photoreceptor bacteriophytochrome could coexist under cryogenic temperatures. However, their populations shift towards the downstream of its reaction pathway as the temperature rises. A numerical deconvolution was needed to isolate the mixed heterogeneous structures.

A truly direct observation of protein structural changes during a reaction or a process demands experiments conducted in a "lights-camera-action!" style. Tremendous efforts at synchrotrons have advanced various techniques of Laue diffraction and time-resolved crystallography, also known as photocrystallography, to capture short-lived structural events that last not even as long as the duration of an electron bunch of a synchrotron, typically 100 ps ($=10^{-10}$ s).

Most recently, ultrafast crystallography has become possible as high peak intensity, ultra-short pulses of hard X-rays as long as femtoseconds (fs=$10^{-15}$ s) are produced by free electron lasers (XFEL) such as the Linac Coherent Light Source (LCLS) at SLAC National Accelerator Lab. We are at a doorstep to direct observations of precursor events of electron and proton transfer, bond formation and rupture, isomerization, and their structural consequences in molecular systems as large as proteins. Mechanistic insights into important processes such as light harvesting, photosynthesis, biomass conversions, visual perception, and various environmental light perceptions rely on direct observations of fundamental chemical and biochemical reactions.

Despite significant progresses in recent years, a stubborn roadblock prevents much wider applications of time-resolved crystallography to many important systems even though light sensitive crystals are available. The chief difficulty arises from a direct conflict between the irreversible nature of many reactions or processes in crystalline states and the necessity of repetitive pump-probe cycles to accumulate signals and to complete a dataset. The technology developed over the past decades based on the classical time-resolved Laue diffraction at synchrotrons is unfortunately only applicable to rapidly reversible reactions, but most important biochemical reactions and biological processes are irreversible in crystalline states for two main reasons. 1) Lattice disorders due to large conformational changes associated with the reaction would significantly degrade the diffraction power of a crystal shortly after the first reaction trigger. 2) Radiation damage to crystals at room temperature also renders a reaction irreversible. Only those organic and protein systems capable of converting rapidly back to their dark states with minimal damage from laser and X-ray pulses have been thus far successfully studied by time-resolved crystallography. XFELs, which promise much greater peak intensity and far better time resolution, could only make this situation of irreversibility more severe by the diffract-and-destroy mode of data collection.

Although time-resolved holography, electron paramagnetic resonance spectroscopy, and coherent diffractive imaging have taken advantages of ultra-short XFEL pulses, numerous attempts at LCLS thus far have not yielded convincing changes in crystallographic electron density maps. Serial crystallography, using a liquid jet to deliver a train of nano to microcrystals into an XFEL beam, has demonstrated in several cases that good electron density maps could be derived from datasets merged from thousands of crystals. The ultra-short XFEL pulses have been exploited to race against radiation damage to nano and microcrystals, but not to capture ultrafast structural actions. While the liquid jet is able to deliver nano and microcrystals of hard-to-grow membrane proteins, it is not compatible with crystals of regular sizes. Nevertheless, the concept of serial crystallography provides an excellent guidance to future dynamic crystallography, except that a robotic delivering system for a large number of regular-sized crystals remains highly desirable.

In stark contrast to the repetitive pump-probe protocol, serial crystallography at room temperature is well suited for studies of irreversible reactions and processes. To accurately acquire difference structural signals, it is critically important to collect a time series of dark and light data points from a single crystal even if one series only covers a small fraction of a complete dataset. At a minimum, one pair of dark and light images is necessary from a same crystal. A large number of crystals would collectively contribute random slices of a complete dataset, each of which spans a full or partial period of a time series. A completely robotic system to deliver thousands of macroscopic crystals into an X-ray beam is a necessary component to achieve dynamic studies via serial crystallography including any ultrafast experiment at XFELs.

SUMMARY OF THE INVENTION

Embodiments of the present invention provide a compact crystallization device for protein (or other macromolecule) and in situ X-ray diffraction data collection, and related methods of utilizing such a device to grow protein crystals and deliver them for in situ X-ray diffraction processes. In embodiments of the present invention, the crystallization device is a mounting chip formed of single crystal quartz or other suitable inorganic crystalline material, such as single crystal silicon, sapphire, etc. Each crystallization chip may be used to deliver hundreds of macroscopic protein crystals into an X-ray beam for in situ diffraction at room temperature, thus achieving serial crystallography for ultrafast dynamic studies. The crystal support chips are unique and innovative in choices of material and fabrication technique to achieve ultralow background scattering. This device is one of the key technologies that will enable crystallographic observations of ultrafast structural changes in proteins.

Some specific technical objectives of the crystallization chips are: The device is compatible with both microbatch and vapor diffusion methods of protein crystallization; it protects against vapor loss during the protein crystallization process over many weeks; it is suitable for visual inspection under a microscope; it is suitable for in situ diffraction at room temperature, that is, it can be inserted directly into an X-ray beam without any step of crystal harvesting and mounting; in an X-ray beam, it contributes very little to background scattering; it carries an on-chip coordinate system for robotic recognition of crystal targets.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, the present invention provides a crystallization device and in situ x-ray diffraction of biological samples, which includes a flat plate made of single crystal quartz, silicon or sapphire and having an array of wells or other patterns defined on the plate. The crystal support device may be in the form of a cover slide which can be used with a crystallization plate (e.g. a Linbro plate) in a vapor diffusion setup.

In another aspect, the present invention provides a method for preparing crystallization of biological samples and x-ray diffraction, which includes the following steps: obtaining a crystal support device made of single crystal quartz, silicon or sapphire; loading a solution containing biological molecules onto the crystallization device; maintaining the solution in a crystal growth environment to grow crystals of the biological molecules; removing the crystallization device carrying the crystals from the crystal growth environment; exposing the crystals carried on the crystallization device to an X-ray beam; and recording X-ray diffracted by the crystal and the crystallization device.

It is to be understood that both the foregoing general description and the following detailed description are exemplary and explanatory and are intended to provide further explanation of the invention as claimed.

BRIEF DESCRIPTION OF THE DRAWINGS

FIGS. 1a-d and 2a-2b compare X-ray diffraction of single crystal quartz with the scattering patterns of other devices and materials typically used for protein crystal growth.

FIGS. 3a-c illustrate a multi-well protein crystal production chip for microbatch or vapor diffusion according to a first embodiment of the present invention.

FIG. 5 illustrates a single crystal quartz chip useful as a cover slide for a crystallization plate for vapor diffusion according to a second embodiment of the present invention.

DETAILED DESCRIPTION OF THE PREFERRED EMBODIMENTS

Figure 2A:
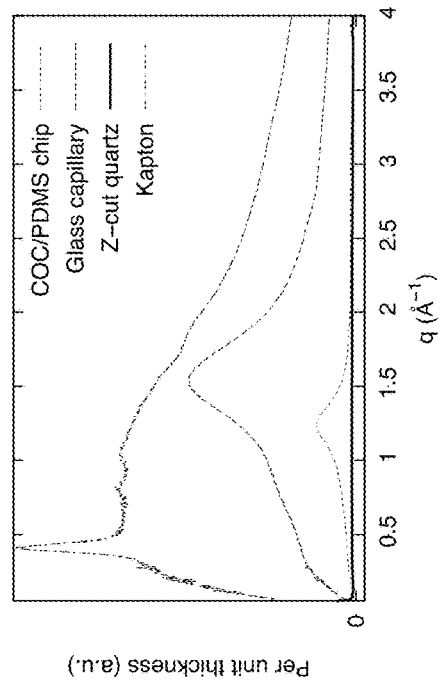

In situ diffraction has been highly desirable in high throughput protein crystallography, such as for drug lead screening, as it bypasses crystal harvesting, a time-consuming step that requires laborious human manipulation. To develop a broadly applicable technology for ultrafast dynamic crystallography, in situ diffraction is not an option, but a prerequisite. An in situ diffraction process requires inserting an intact thin chip, carrying protein crystals that have been grown on the chip, into an X-ray beamline for room temperature diffraction without crystal harvesting and mounting. Many in situ experiments have been carried out at synchrotrons with standard or special crystallization plates, examples including: Axford, D. et al., In situ macromolecular crystallography using microbeams, Acta Cryst. (2012) D68, 592-600; Bingel-Erlenmeyer, R. et al., SLS Crystallization Platform at Beamline X06DA—A Fully Automated Pipeline Enabling in Situ X-ray Diffraction Screening, Cryst. Growth Des. 2011, 11, 916-923; Jacquamet, L. et al., Automated Analysis of Vapor Diffusion Crystallization Drops with an X-Ray Beam, Structure, Vol. 12, 1219-1225, July, 2004; Kisselman, G. et al., X-CHIP: an integrated platform for high-throughput protein crystallization and on-the-chip X-ray diffraction data collection, Acta Cryst. (2011) D67, 533-539; and le Maire, A. et al., In-plate protein crystallization, in situ ligand soaking and X-ray diffraction, Acta Cryst. (2011) D67, 747-755. These in situ diffraction experiments are limited to identification of salt crystals, crystal screening, or other qualitative observations. The vast majority of data collection remains at cryogenic temperatures from manually harvested crystals. The major difficulty of in situ diffraction is high background scattering from non-crystalline materials in the X-ray beam path. Their cumulative path length is often far longer than that through a protein crystal. Although background scattering could be digitally subtracted from a diffraction image, there is no statistical gain in terms of signal-to-noise ratio. Strategies to minimize background scattering include use of microbeams, beams with low divergence, large area detector, and long distance from sample to detector, none of which changes the root cause of high background.

Numerous efforts have been made to design thin devices for protein crystallization and to seek relatively X-ray transparent materials for such devices, examples including: Dhouib, K. et al., Microfluidic chips for the crystallization of biomacromolecules by counter-diffusion and on-chip crystal X-ray analysis, Lab Chip, 2009, 9, 1412-1421; Gerdts, C. et al., The plug-based nanovolume Microcapillary Protein Crystallization System (MPCS), Acta Cryst. (2008) D64, 1116-1122; and Hansen, C. et al., A Microfluidic Device for Kinetic Optimization of Protein Crystallization In Situ Structure Determination, J. AM. CHEM. SOC. 2006, 128, 3142-3143; and Perry, S. et al., Microfluidic Generation of Lipidic Mesophases for Membrane Protein Crystallization, Crystal Growth & Design, Vol. 9, No. 6, 2009, 2566-2569. The dilemma faced is background scattering during diffraction versus vapor permeability for crystal growth. Thin films of various types of polymers, with thickness comparable to the size of a protein crystal (tens of μm), are often permeable to water vapor to various extents, and therefore inadequate for crystallization devices that must last days or even weeks for crystal growth. Materials like cyclic olefin copolymer (COC) of 100 μm or thicker give rise to sizable background scattering and still permit noticeable vapor loss over days.

According to embodiments of the present invention, a crystallization chip is made of single crystal quartz (α quartz). This material diffracts X-rays much stronger than a protein crystal and leads to an overlay of diffraction patterns from both the single crystal quartz and protein crystals. However, the very small unit cell (~5 Å) of single crystal quartz results in very few Bragg peaks within the resolution range of protein diffraction. These Bragg peaks could be completely avoided by alignment of the device with respect to the incident X-ray beam (FIG. 1a). This pure monocrystalline material generates virtually no diffuse scattering, therefore gives rise to ultralow background. Like glass, intact single crystal quartz serves as a very good vapor barrier even with a thickness as thin as μm.

Single crystal quartz diffractions can be compared with the scattering patterns of other devices and materials, as shown in FIGS. 1a-1d. The diffraction pattern in FIG. 1a shows that a well-aligned Z-cut quartz crystal (cut surface perpendicular to Z-axis) can avoid major Bragg peaks completely. FIG. 1b shows a diffraction pattern from a slightly misaligned Z-cut quartz crystal. Strong reflections can occur at a high Bragg angle, but diffuse scattering from the quartz crystal is minimal. In contrast, a commonly used thin-wall glass capillary and a low profile crystallization chip made of COC and polydimethylsiloxane (PDMS) generate much higher background from equal amount of X-ray exposure (see FIG. 1c and FIG. 1d, respectively). A crystallization device of 50 μm thick fabricated from a quartz crystal produces virtually no background (see FIG. 2a). The scattering profiles normalized to unity in thickness also show extremely low background scattering compared with other devices and materials (see FIG. 2b).

In FIGS. 1a-1d, all scattering images were collected under the same condition, including exposure time and sample-to-detector distance. All images were rendered with the same software settings. The resolution at the edge of the detector is 1.4 Å. In FIG. 1a, the thickness of the quartz crystal was 250 μm. In FIG. 1c, the empty thin-wall glass capillary had a manufacture specification stated wall thickness of 10 μm. In FIG. 1d, the COC/PDMS crystallization chip had a total thickness of 280 μm.

Figure 2B:
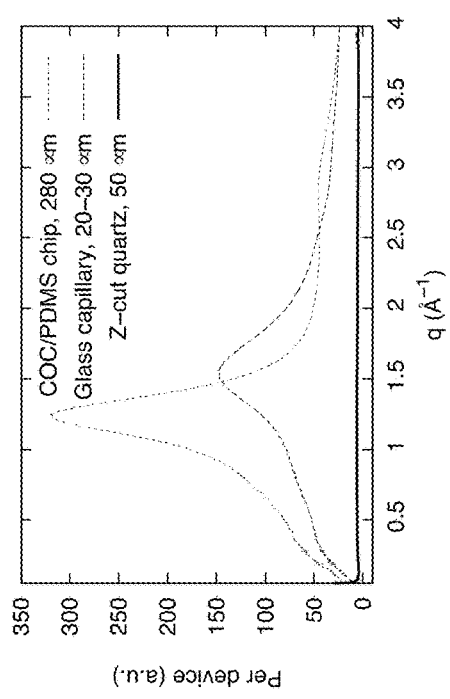

FIGS. 2a-2b show scattering curves of single crystal quartz and other devices. Cylindrically averaged scattering intensities are plotted as function of scattering vector q. In order to show the scattering curve of single crystal quartz, zero of each vertical axis is up-shifted. In FIG. 2a, the scattering intensity of single crystal quartz has been scaled back to a thickness of 50 μm, and compared to those of the other devices. In FIG. 2b, the scattering intensities have been normalized to unity in thickness and compared.

According to embodiments of the present invention, thin single crystal quartz chips with etched wells are used as crystallization devices for holding protein crystals during X-ray diffraction data collection. In these embodiments, the crystallization devices are the original place the protein crystals grow. The crystallization devices may be designed in many forms to suit different applications. One example is a single crystal quartz chip with an array of wells having a predefined bottom thickness, where protein crystals are grown in the wells. Two other examples are single crystal quartz chips with a plurality of wells that can be used as a cover slide (also called coverslip) for common crystallization plates such as 24-well Linbro plates. These examples will be described in more detail below.

Figure 3A:
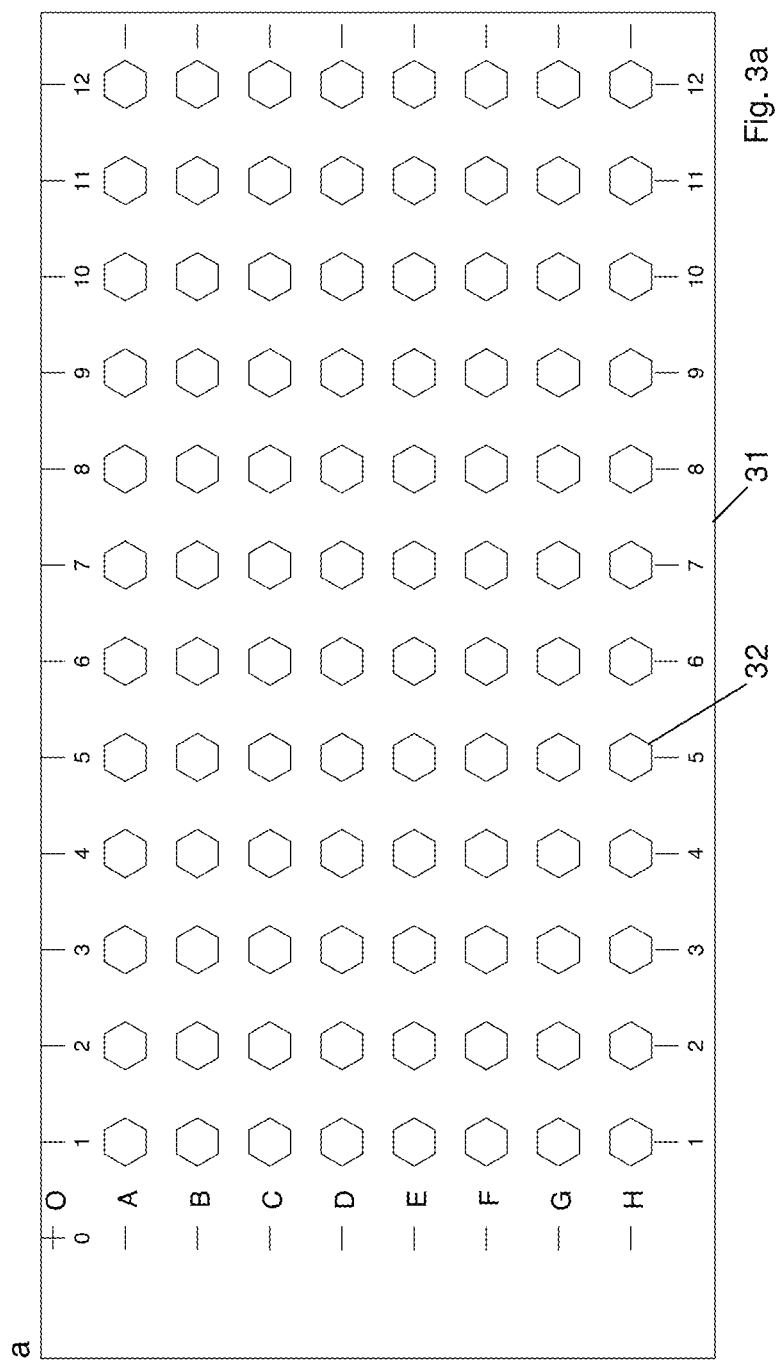

FIGS. 3a-3c illustrate a design of a multi-well protein crystal production chip for microbatch or vapor diffusion according to a first embodiment of the present invention. The single crystal quartz chip 31 is a thin plate with two parallel surfaces which are preferably perpendicular to the Z-axis of the quartz crystal. FIG. 3a is a schematic top view of the layout of 96 wells 32 on a 2" (diagonal) chip 31. The numbers and letters shown in FIG. 3a are engraved markings which are preferably provided on the chip 31 for the purpose of identifying the wells 32. The extra space on the left of the chip 31 is preferably provided for handling and mounting of the chip. FIG. 3b is a detailed top view of a well 32. Preferably, each well is a hexagon due to the trigonal symmetry of quartz crystal and is oriented such that one pair of sides is parallel to the X- or Y-axis. FIG. 3c is a side cross-sectional view of a well 32 taken in the cross-section C-C' of FIG. 3b. The thickness of the bottom 32a of the wells 32 is preferably less than 50 μm. In one example, the overall size of the chip 31 is 45 by 22 mm, and the size of the wells 32 (diagonal of the hexagon) is about 1.6 mm. The capacity of each such well 32 is 0.16 μl per 100 μm depth. The total thickness of the chip 31 may be 100 to 300 μm. These sizes are only given here as examples; other sizes may be used. More generally, the chip 31 may be 10 to 100 mm by 10 to 50 mm, and the wells may be 0.5 to 5 mm in size. The wells may also have other shapes, such as polygons with unequal sides, elongated grooves, etc.

While in the illustrated embodiment two parallel flat surfaces of the single crystal quartz plate are perpendicular to the Z-axis, other orientations may be used. For example, X-cut quartz (with the two parallel flat surfaces perpendicular to the X-axis) may be advantageous for etching long channels.

For microbatch crystallization, after the wells 32 of a protein crystal production chip 31 are loaded with appropriate protein solutions, another identical chip is used as a cover and sealed with the first chip by oil or grease, and crystals will grow inside the wells. Alternatively, a thin flat single crystal quartz plate can be used as the cover. For vapor diffusion crystallization, a protein crystal production chip 31 loaded with protein solution in its wells is placed inside a sealed container with a shared reservoir of crystallization solution or one reservoir for each column of wells. After crystal growth, each fully loaded chip 31 can contain hundreds of protein crystals for in situ diffraction.

In a second embodiment of the present invention, a single crystal quartz chip is designed to be used as a cover slide for a crystallization plate, such as a 24-well Linbro plate.

Figure 6:
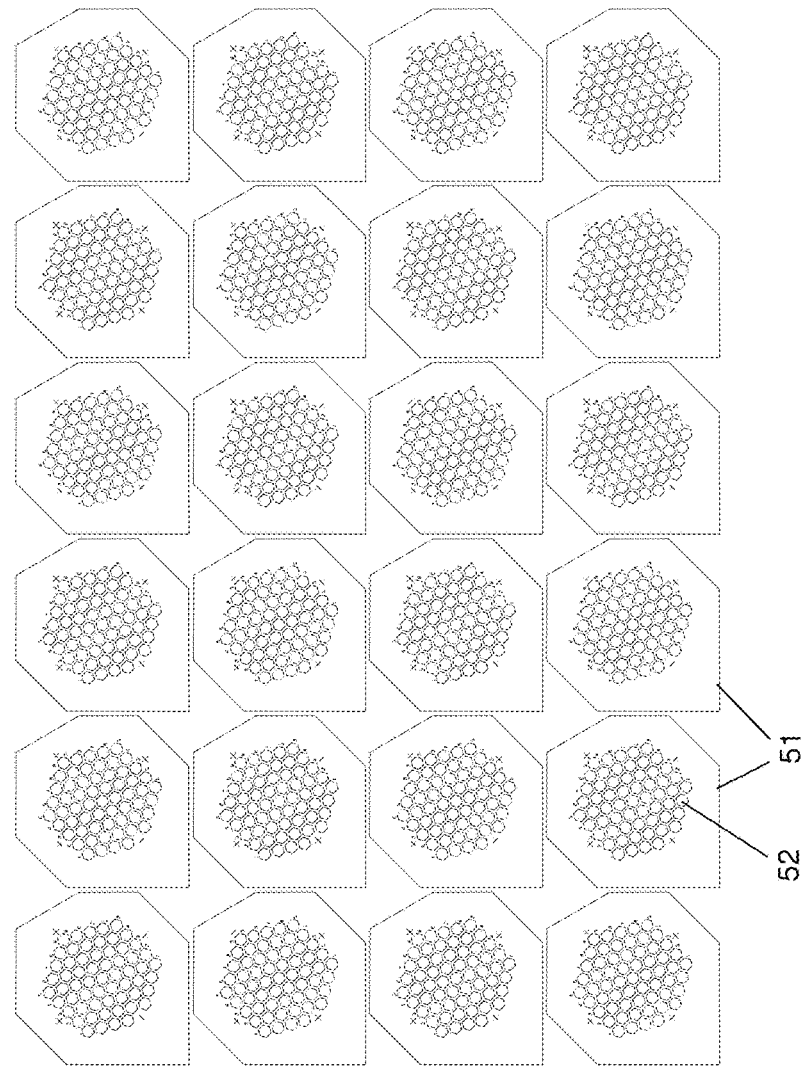
FIG. 6 schematically illustrates a layout of 24 single crystal quartz chips of FIG. 5 on a 24-well crystallization plate.

24-well Linbro plates made of clear, rigid polystyrene are one of the most popular platforms for protein crystallization, e.g. using hanging drop vapor diffusion method. The Linbro plate is a tray, approximate 15.0 cm by 10.8 cm by 2.2 cm in size, having a 4 by 6 array of wells. Each well is cylindrical shaped, approximately 1.7 cm in diameter and 1.6 cm deep. Each well has a wide, raised ring around it forming a flat rim, which allows each individual well to be sealed using grease or oil and a cover slide. Conventional cover slides used with Linbro plates, made of glass or plastic, are typically a 22 mm round or square shape that covers a well of the plate. According to the present embodiment, a single crystal quartz chip replaces the commonly used glass coverslip from where one or several protein solution drops hang over each well of crystallization reservoir solution. FIG. 6 schematically illustrates a layout of 24 single crystal quartz chips 51 on a 24-well Linbro plate (the plate itself is not shown). In this example, the single crystal quartz chips 51 are sized properly for the Linbro plate; e.g., they are smaller than a 22 mm square and larger than a 1.7 mm diameter circle.

FIG. 5 shows a top view of a chip 51 in detail. The chip 51 is a piece of intact monocrystalline quartz, which performs as an excellent vapor barrier as good as a conventional cover glass. The chip 51 is made of a Z-cut α quartz wafer, that is, with Z-axis perpendicular to the two parallel surfaces of the wafer. The chip 51 is approximately 250 μm thick. The asymmetric shape of the chip 51 shown in FIG. 5 is designed to maintain a common orientation among all chips with respect to the quartz crystal lattice; other shapes may be used as well. A number of (60 in this example) hexagonal wells 52 are formed in the center area of the chip 51 to hold protein solution for crystallization. The shape of the wells 52 is generally the same as that of the wells 32 shown in FIGS. 3b and 3c. The wells 52 are approximately 1.6 mm in size (diagonal of the hexagon), and the bottom of the wells are approximately 25 μm thick. The distance between adjacent wells 52 is approximately 0.3 mm. These sizes are only given here as examples, and other sizes may be used. More generally, the thickness of the chip 51 may be between 100 and 300 μm; the thickness of the bottom of the wells 52 may be less than 50 μm, and the size of the wells may be 0.5 to 5 mm. The wells may also have other shapes, such as polygons with unequal sides, elongated grooves, etc.

A single crystal quartz chip 51 loaded with protein solution in its wells 52 may be used as a coverslip in a vapor diffusion crystallization setup. In such a setup, the chip 51 is flipped over so the wells 52 of the chip 51 face downwards, and the chip 51 is placed over the well of the Linbro plate which contains a crystallization solution and acts as a reservoir, with the wells 52 facing the crystallization solution. Vacuum grease or oil is usually used to seal between the edges of the chip 51 and the reservoir well of the Linbro plate. After a crystal growth period of days to weeks, protein crystals form in the wells 52 of the single crystal quartz chip 51 and are ready for X-ray diffraction data collection.

Figure 7:
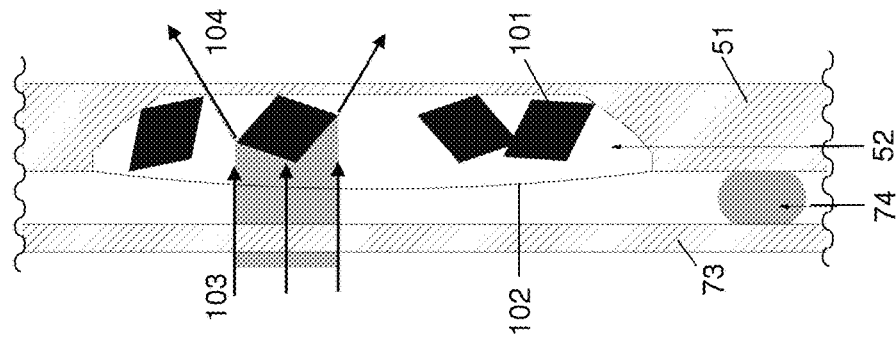
FIG. 7 schematically illustrates a part of a chip sandwich using the single crystal quartz chip of the second embodiment, assembled for X-ray diffraction data collection.

FIG. 7 schematically illustrates a part of a chip sandwich assembled for X-ray diffraction data collection. The chip 51 is removed from the Linbro plate which breaks the vacuum seal. Another thinner flat single crystal quartz chip 73, of an identical shape and orientation as chip 51 but preferably with no wells 52, immediately covers the first chip 51 that carries protein crystals. The residual vacuum grease 74 on the first chip 51 is typically sufficient to seal the two chips together. As a result, the protein crystals are sandwiched between two single crystal quartz chips of identical orientations, forming a chip sandwich. This process can be completed in a few seconds. This chip sandwich is ready for X-ray diffraction experiment at room temperature. The entire procedure achieves quasi-in-situ diffraction, throughout which the protein crystals are not manipulated directly.

As shown in FIG. 7, due to the grease 74 between two chips 51 and 73, the chips will not be in contact with each other, but have an air gap in between, and the drop of crystallization solution 102 and the crystals 101 in the well 52 are not disturbed. The thickness of the air gap may vary. In case of a very thin air gap, the cover chip 73 may be in contact with some crystallization drops 102, which may disturb the crystals 101 in them. In such a case, additional grease may be used to increase the gap size.

For a single crystal quartz chip 51 of the second embodiment, the nominal capacity of each etched well 52 is 350 nL, thus the total capacity is 21 μL per chip. However, actual loadings from a small fraction to several times of the nominal capacity are possible. After each chip 51 is loaded with a protein solution, it is turned over and placed over a greased Linbro plate well to cover a well of reservoir solution. The heptagon shape of the chip 51 (see FIGS. 5 and 6), which can be viewed as a rectangle (preferably a square) with three corners cut off, is designed for easy placement and removal, as the corners will not come too close against each other when a Linbro plate is fully loaded for crystal production (FIG. 6). If a protein can be successfully crystallized using a conventional hanging drop method, it should be able to crystallize using the single crystal quartz chip 51 of the present embodiment without significant modification to the crystallization protocol.

In the example shown in FIG. 5, four cross symbols (+) are engraved on the backside of the chip 51 and flank the etched wells 52 on four sides. Each symbol is about 15 mm from the opposite one. These cross symbols define an on-chip coordinate system. During or after crystallization, a Linbro plate can be place on a computer driven translational stage under an optical microscope for observation or automated crystal recognition. The opposite cross symbols define two orthogonal linear ranges from −1 to +1. Therefore, all crystals on the chip 51 can be recorded within a two-dimensional range from (−1, −1) to (+1, +1). These marked positions can be used later during automated data collection. Even if scaling error and difference in mounting may exist between offline and online systems, the on-chip fractional coordinate system helps to cancel out potential systematic errors.

For X-ray diffraction data collection, the assembled chip sandwich may be mounted in a clamp. The clamp may have two jaws which are flat plates disposed parallel to each other, with a V-shaped thin slot between them so that the 90 degree corner of the chip sandwich can be inserted into the slot vertically. The gap between two jaws (i.e. the thickness of the slot) of the clamp can be made adjustable by several screws. One or both jaws may be lined with velvet or other fabric to provide soft clamping on the chip. The chip clamp also has a pin as a handle, preferably compatible with the standard ⅛ inch pin used in X-ray diffraction equipment so that the chip sandwich can be mounted for diffraction experiments at X-ray sources such as synchrotron beamlines.

During X-ray diffraction data collection, the cover chip 73 of the chip sandwich, which carry no protein crystals, should face the incident X-ray beam (see FIG. 7), since it is usually thicker than the bottom of the etched well 52 of the base chip 51. The thinner bottom of wells will absorb less from the diffracted rays from the protein crystal, thus resulting in stronger signal. Along the X-ray beam path, the quartz crystals of the base chip 51 and cover chip 73 diffract much stronger than the protein crystal, but there are only very few diffraction spots within the resolution range of typical protein diffraction. When the single crystal quartz chips are well aligned with their Z-axes along the X-ray beam, strong Bragg reflections from single crystal quartz can be completely avoided. It is important that the base and cover chips 51 and 73 share approximately the same orientation. As a result, the Bragg reflections will superimpose at the same locations on the detector. It can be shown that if the chips are well aligned, the first small possibility to encounter a Bragg reflection is at 1.5-1.6 Å resolution using X-ray source around 12 keV depending on the exact X-ray wavelength. This is already considered a high resolution for protein diffraction. Only a small fraction of protein crystals would reach this high resolution. If protein diffraction does not reach 1.5-1.6 Å resolution, the accuracy of the chip alignment would tolerate ±6.7°, which would provide a window to collect rotational diffraction data between ±5°. The first encounter of Bragg reflection from quartz crystal is at 4.3 Å resolution, if the chip orientation exceeds this range. Other than several Bragg reflections, quartz crystals produce very little diffuse scattering. The remaining background producing materials in the X-ray path are the liquid surrounding the protein crystal, bulk water in the lattice of the protein crystal, and air. Diffraction images with clean background can be derived from such a device.

Another advantage of single crystal quartz chips is that the material feels much like glass and is reusable. After use, disassembled base and cover chips can be placed on a rack and soaked in water or an organic solvent for cleaning. Ultrasonic cleaning can also be applied. Manual brush is also possible if necessary. The chips can be air dried after rinses with distilled water. The strength of monocrystalline quartz permits multiple reuses of the chips under normal conditions.

Figure 8:
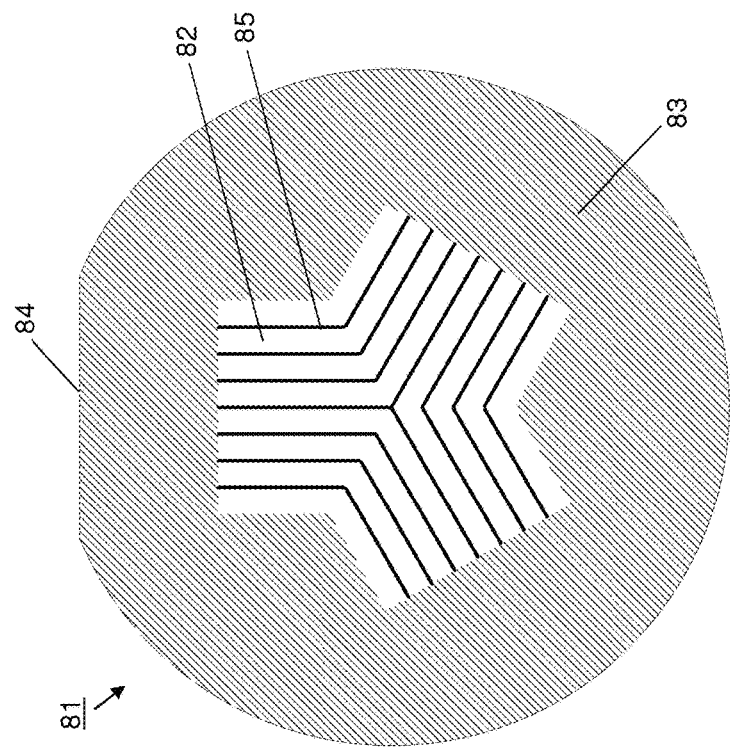
FIG. 8 illustrates another single crystal quartz chip useful as a cover slide for a crystallization plate for vapor diffusion according to a third embodiment of the present invention.

FIG. 8 shows a circular single crystal quartz chip according to a third embodiment of the present invention. It can be used for both hanging drop vapor diffusion and batch methods of protein crystallization. The circular chip 81 is made of a Z-cut α quartz wafer. The diameter is about 1 inch, slightly larger than an individual well of the Linbro plate. The outer area 83 (indicated by shading) is 250 µm thick. The wells 82 located in the center area are etched to about 25 µm in thickness at the bottom. The wells 82 are in the shape of multiple parallel lanes separated by walls 85. In one implementation, the walls are about 250 µm thick and the lanes are about 750 µm wide. One function of the walls 85 is to provide structural support for the wells, to avoid forming an overly large area with a thin bottom. The Y-shaped three fold symmetric pattern of the wells 82, i.e. three sets of parallel lanes oriented 120 degrees with respect to each other, follows the inherent trigonal symmetry of the quartz crystal. The pattern is aligned to a straight side edge 84 of the wafer that is cut to indicate the X-axis.

This chip 81 can be used in the same way as the chip 51 of the second embodiment. When the etched wells 82 are loaded with protein solution, the chip is then used as a coverslip the same way as in normal vapor diffusion crystallization. Alternatively, either a flat wafer or another identical chip can be used to seal the protein solution for batch crystallization. After protein crystals reach the mature size, the chip is flipped over and covered with a flat wafer or another chip. Protein crystals sandwiched between two single crystal quartz chips are ready for diffraction experiments.

Figure 9:
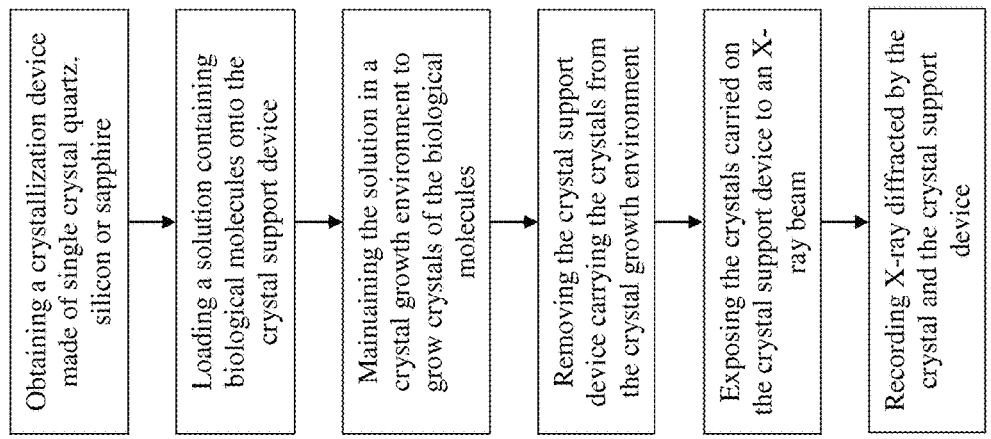
FIG. 9 shows a method for preparing biological samples for crystallization and x-ray diffraction according to various embodiments of the present invention.

More generally, as shown in FIG. 9, a method for preparing biological samples for crystallization and x-ray diffraction includes: obtaining a crystallization device made of single crystal quartz, silicon or sapphire; loading a solution containing biological molecules onto the device; maintaining the solution in a crystal growth environment to grow crystals of the biological molecules; removing the crystallization device carrying the crystals from the crystal growth environment; exposing the crystals carried on the device to an X-ray beam; and recording X-ray diffracted by the protein crystals (the recorded X-ray signal will include diffracted X-ray from the crystallization device, if any).

The single crystal quartz chips 31, 51, 81 in the above embodiments can be manufactured by employing known technologies. Single crystal quartz is commonly used for its piezoelectric and optical properties. Synthetic single crystal quartz is commercially produced under controlled temperature and pressure. A wafer can be sawed at a specific orientation with respect to the crystal lattice for a particular application. Many differently sawed wafers are commercially available. Thin wafers of various thicknesses down to 50 µm can be sawed and polished. Z-cut cc quartz wafers of various thicknesses and sizes are commercially available. The X-ray diffraction application in embodiments of the present invention requires only low-grade single crystal quartz wafers of modest sizes.

Although the chemical composition of single crystal quartz is largely identical to that of glass, the technique of ultrafast laser enhanced glass etching does not apply to monocrystalline quartz. Chemical wet etching with hydrofluoric acid HF buffered by ammonium fluoride NH4F is effective for crystalline quartz. Etching on different surfaces of quartz crystal demonstrated very anisotropic behaviors. The rates of wet etching on many crystallographic planes have been well studied. It has been shown that the fastest etching rate is along the Z-axis. Therefore, in preferred embodiments of the present invention, Z-cut quartz wafer are used and shallow triangular or hexagonal wells are etched on the wafer. In such a case the well bottom is a flat Z plane (see FIG. 3c). Photolithography is a mature technique to create masks of fine details over single crystal quartz wafers so that only desired areas are etched by chemicals. The slow etching rate at about 30 µm/hr at 50° C. allows fine control of the bottom thickness. It has been demonstrated that a remaining membrane as thin as 3.5 µm could be achieved. In preferred embodiments of the present invention, the wells 32, 52, 82 of the single crystal quartz chip 31, 51, 81 have a bottom of 10 to 50 µm in thickness, which can be readily achieved using known technologies.

Figure 4A:
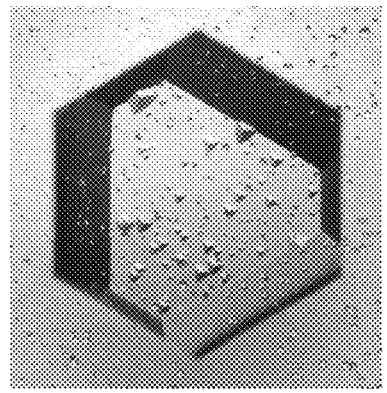
FIGS. 4a-b show a computer simulation and a micrograph, respectively, of an etched well in a single crystal quartz chip according to embodiments of the present invention.
Figure 4B:
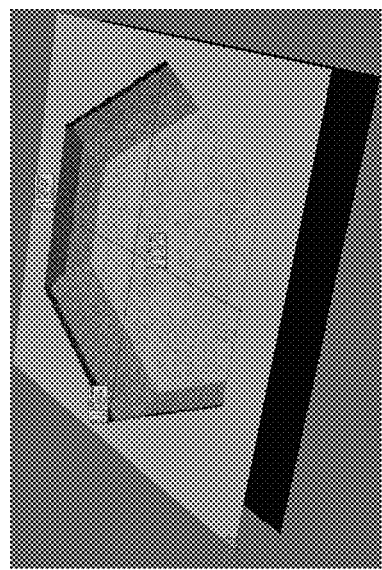

FIGS. 4a and 4b show a computer simulation and a micrograph, respectively, of an etched well. In the micrograph shown in FIG. 4b, the small triangular shapes in the well are residuals from premature finish of etching, which may be minimized, as the etching condition is further refined. Other than the harmless minor defect, the actual fabrication result matches with theoretical simulation of etching quite well (FIG. 4a).

Embodiments of this invention provide a new platform of serial crystallography that efficiently introduces macroscopic protein crystals into an X-ray beam. This technology plays a comparable role of the liquid jet that shoots nano to microcrystals of hard-to-grow membrane proteins in liquid capsules into an X-ray beam. Here thousands of macroscopic crystals can be delivered directly using the crystallization chip according to embodiments of the present invention without additional steps of crystal harvesting and mounting. The crystallization chip is designed for ultrafast dynamic crystallography that uses a large number of regular sized crystals. This is an enabling technology to study ultrafast but irreversible reactions and processes at atomic resolution. Findings from ultrafast dynamic studies will allow biologists to visualize how chemical reactions start and proceed in proteins. The resulting mechanistic understandings will enable further developments to achieve sophisticated control, manipulation, and utilization of biological processes such as light harvesting, photosynthesis, biomass conversion, vision, and environment sensing.

In addition to single crystal quartz, other materials that may be used to form the crystallization device include single crystal silicon, sapphire, etc. Each of these materials has its unique character that may be advantageous for specific applications. Single crystal quartz wafers are commercially available and relatively less expensive. Thin silicon wafers are transparent to UV light but not to visible light, which may have its usage for light sensitive proteins.

Although the crystallization device and related methods are described above in the context of protein crystallography, i.e. the study of protein crystals using X-ray diffraction, these devices and related methods can also be used in crystallography study of other macromolecules and other biological or non-biological samples that can be crystallized.

It will be apparent to those skilled in the art that various modification and variations can be made in the crystallization chip for X-ray diffraction in protein crystallography and related methods of the present invention without departing from the spirit or scope of the invention. Thus, it is intended that the present invention cover modifications and variations that come within the scope of the appended claims and their equivalents.

What is claimed is:

1. A crystallization device for in situ x-ray diffraction of biological samples, comprising:
   a first flat plate made of single crystal quartz, single crystal silicon or single crystal sapphire and having a plurality of wells defined on the plate;
   a second flat plate made of single crystal quartz, single crystal silicon or single crystal sapphire disposed to cover the first flat plate with an air gap between the first and second plates; and
   a sealing material disposed between the first plate and the second plate to seal them together to define a sealed space formed by the air gap for holding the samples.

2. The crystallization device of claim 1, wherein the first plate is made of single crystal quartz, and wherein two parallel surfaces of the first plate and a bottom surface of the wells are perpendicular to a Z-axis of the quartz crystal.

3. The crystallization device of claim 2, wherein the first plate has a thickness of between 100 and 300 μm, and the wells have a bottom thickness of less than 50 μm.

4. The crystallization device of claim 2, wherein each well is a hexagon with one pair of sides parallel to an X- or Y-axis of the quartz crystal, and a diagonal of the hexagon is between 0.5 and 5 mm.

5. The crystallization device of claim 2, wherein the wells are multiple parallel lanes.

6. The crystallization device of claim 1, wherein the first plate and the second plate each has a size smaller than a 22 mm square and larger than a 1.7 mm diameter circle and a heptagon shape.

7. The crystallization device of claim 1, wherein the first plate is made of single crystal quartz, wherein two parallel surfaces of the first plate and a bottom surface of the wells are perpendicular to a Z-axis of the quartz crystal, wherein the first plate has a substantially circular shape having a diameter of about 1 inch with one straight edge parallel to an X-axis of the quartz crystal, and wherein the wells have a Y-shaped three fold symmetric pattern with one branch of the Y-shape perpendicular to the straight edge.

8. The crystallization device of claim 1, wherein the first plate further includes engraved markings indicating a coordinate system for identifying each well.

9. The crystallization device of claim 1, wherein the second plate has two parallel surfaces and is free of wells.

10. The crystallization device of claim 1, wherein the first plate and the second plate are made of the same material and have substantially identical crystal orientations.

11. The crystallization device of claim 2, wherein the second plate is made of single crystal quartz, and wherein two parallel surfaces of the second plate are perpendicular to a Z-axis of the quartz crystal.

12. A crystallization device for in situ x-ray diffraction of biological samples, comprising:
   a plate made of single crystal quartz and having a plurality of wells defined on the plate, wherein two parallel surfaces of the plate and a bottom surface of the wells are perpendicular to a Z-axis of the quartz crystal, wherein the plate has a substantially circular shape having a diameter of about 1 inch with one straight edge parallel to an X-axis of the quartz crystal, and wherein the wells have a Y-shaped three fold symmetric pattern with one branch of the Y-shape perpendicular to the straight edge.

* * * * *